United States Patent
Leobal et al.

(10) Patent No.: US 9,288,447 B2
(45) Date of Patent: Mar. 15, 2016

(54) HOLDING DEVICE FOR VISUALLY INSPECTING A TIRE

(75) Inventors: Christian Leobal, Veyre-Monton (FR); Gérard Bor, La Roche Noire (FR)

(73) Assignees: COMPAGNIE GENERALE DES ETABLISSEMENTS MICHELIN, Clermont-Ferrand (FR); Michelin Recherche et Technique S.A., Granges-Paccot (CH)

( * ) Notice: Subject to any disclaimer, the term of this patent is extended or adjusted under 35 U.S.C. 154(b) by 715 days.

(21) Appl. No.: 13/635,618

(22) PCT Filed: Mar. 4, 2011

(86) PCT No.: PCT/EP2011/053278
§ 371 (c)(1),
(2), (4) Date: Feb. 1, 2013

(87) PCT Pub. No.: WO2011/113711
PCT Pub. Date: Sep. 22, 2011

(65) Prior Publication Data
US 2013/0128029 A1 May 23, 2013

(30) Foreign Application Priority Data
Mar. 15, 2010 (FR) ..................... 10 51828

(51) Int. Cl.
*B60C 25/14* (2006.01)
*H04N 7/18* (2006.01)
(Continued)

(52) U.S. Cl.
CPC ............... *H04N 7/18* (2013.01); *B60C 25/125* (2013.01); *B60C 25/138* (2013.01); *B60C 25/14* (2013.01);
(Continued)

(58) Field of Classification Search
CPC .... B60C 25/14; B60C 25/142; B60C 25/138; B60C 25/125
USPC .......... 378/58, 61; 254/50.1, 50.2, 50.3, 50.4; 396/19; 382/141; 29/894.31, 894.3, 29/221.5; 73/146, 146.2, 146.3, 146.4
See application file for complete search history.

(56) References Cited

U.S. PATENT DOCUMENTS 1,647,054 A * 10/1927 Price ..................... B60C 25/142
254/50.2
1,886,834 A * 11/1932 Prentice ................ B60C 25/142
254/50.2

(Continued)

FOREIGN PATENT DOCUMENTS

JP 2010-032467 2/2010

*Primary Examiner* — Monica Carter
*Assistant Examiner* — Mahdi H Nejad
(74) *Attorney, Agent, or Firm* — Cozen O'Connor (57) ABSTRACT

A for inspecting the internal surface located between a first and a second bead of a tire (P), comprising means for acquiring the image of the internal surface (1) of the tire, and centering means that are able to lock the first bead around its entire circumference on a reference plate, and to set the tire into relative rotation about its axis XX' with respect to said image acquisition means. This device comprises means for opening and for holding the second bead, said means comprising two internal holding rollers (32, 32) which have a generally radial axis, and at least one external holding roller (33) which has a generally radial axis, is disposed substantially in the middle of the angular sector formed by the two internal holding rollers (31, 32) and is able to come into abutment against the external part of said second bead, the internal (31, 32) and external (33) holding rollers being mounted so as to rotate as one about the axis XX' of said image acquisition means (1).

14 Claims, 5 Drawing Sheets (51) Int. Cl.
   *B60C 25/138*   (2006.01)
   *B60C 25/125*   (2006.01)
   *G01M 17/02*    (2006.01)
   *G01N 21/954*   (2006.01)

(52) U.S. Cl.
   CPC ........... *B60C 25/142* (2013.01); *G01M 17/021* (2013.01); *G01M 17/027* (2013.01); *G01N 21/954* (2013.01)

(56) References Cited

U.S. PATENT DOCUMENTS

| | | | |
|---|---|---|---|
| 2,035,972 A * | 3/1936 | Mangel | B60C 25/142 254/127 |
| 2,347,311 A * | 4/1944 | Branick | B60C 25/142 254/50.4 |
| 2,850,263 A * | 9/1958 | Hawkinson | B29D 30/64 254/50.3 |
| 3,830,469 A * | 8/1974 | Oaks, Jr. | B60C 25/142 254/50.3 |
| 4,160,537 A * | 7/1979 | Severson | B60C 25/142 254/50.3 |
| 4,171,794 A * | 10/1979 | Haskell | B60C 25/142 254/50.1 |
| 5,165,273 A * | 11/1992 | Church | B60C 25/002 254/50.2 |
| 7,076,876 B2 * | 7/2006 | Baumgartner | B60C 25/00 29/894.3 |
| 7,360,410 B2 | 4/2008 | Steinbichler et al. | |
| 7,387,019 B2 * | 6/2008 | Shaw | G01M 17/027 254/50.2 |
| 8,613,303 B1 * | 12/2013 | Hanneken | B60C 25/138 157/1.17 |
| 8,770,254 B1 * | 7/2014 | Hanneken | B60C 25/138 157/1.17 |
| 2006/0254725 A1 * | 11/2006 | Gonzaga | B60C 25/0578 157/1.17 |
| 2008/0066532 A1 | 3/2008 | Shaw et al. | |
| 2008/0173408 A1 * | 7/2008 | Vignoli | B60C 25/0527 157/1.24 |
| 2011/0188731 A1 * | 8/2011 | Sekiguchi | G01B 11/30 382/141 |
| 2014/0132740 A1 * | 5/2014 | Clark | G01M 17/027 348/48 |

* cited by examiner

HOLDING DEVICE FOR VISUALLY INSPECTING A TIRE

RELATED APPLICATIONS

This is a U.S. National Phase Application under 35 USC 371 of International Application PCT/EP20111053278 filed on Mar. 4, 2011.

This application claims the priority of French Application No. 10/51828 filed Mar. 15, 2010, the content of which is hereby incorporated by reference.

FIELD OF THE INVENTION

The invention relates to the field of the manufacture of tires, and more particularly the field of visually checking the latter during or at the end of the production process.

BACKGROUND OF THE INVENTION

Visual inspection of tires is widespread in the tire industry and very frequently still relies upon the dexterity of the operators responsible for detecting any visible imperfections on the surface of the tire. To this end, numerous means of assistance have been developed for handling and making visible regions that are particularly inaccessible, such as the internal part of the tire.

The function of these means is to keep the beads of the tire in the open or spaced-apart position and to set the tire in rotation, as is described by way of example in the publication U.S. Pat. No. 4,160,537.

As the processing power of computing means increases, manufacturers have now foreseen the possibility of automating these checking tasks. To this end, lighting and digital imaging means have been introduced into the internal part of the tire in order to define the image and the internal relief. This digital image is then processed by suitable computing means and compared with a reference image so as to determine any anomalies in the surface of the tire.

The invention is aimed more particularly at the means for holding and rotating the tire during the phase of acquiring the image of the internal part of the tire.

This means has to be able to keep the tire in the open position while ensuring good geometric precision. Moreover, it must allow the lighting and image acquisition means to pass through while ensuring a relative movement of said acquisition means with respect to the tire.

Means dedicated to this function have been disclosed, by way of example, in the publication US200810066532. The apparatus described comprises a plurality of pairs of hooks, or of paws, which are aligned vertically and are intended to move apart the beads and to keep the tire in the open position. These paws rotate about an axis between an engaged position and a folded back position in order to allow the introduction and removal of the tire into and from the device.

However, this type of apparatus presents two types of problem. Specifically, although the number of pairs of paws is not limited, it can be seen that the bead deforms between two successive holding paws, and this has the effect of causing waves in the shape of the lower and upper beads with respect to the plane of the bead perpendicular to the axis of the tire, and of substantially modifying the geometry of the actual tire with respect to a theoretical image. A second drawback comes from the fact that the holding paws are fixed with respect to the bead and prevent those parts of the bead on which they rest from being imaged.

SUMMARY OF THE INVENTION

One object of the invention is to remedy these two drawbacks by providing a holding means that is able to preserve the geometry of the beads in a precise and repetitive manner and is able to accommodate imaging means.

The device according to an embodiment of the invention utilizes the fact that the visualization means are generally designed to inspect an angular region which is limited, and even limited to a line realized by the width of a slot or of a laser beam. The complete image is then obtained by adding together all of the images of circumferential portions by rotating the tire about its axis with respect to the image acquisition means. It is therefore appropriate to control the geometric position of just the illuminated region which is being imaged.

The device according to an aspect of the invention comprises:

means for acquiring the image of the internal surface of the tire, said means being formed by lighting means and one or more cameras and being able to pass into the space inside the tire and to produce the image of an angular region of given angle of the internal surface of the tire, centering means that are able to lock a first bead around its entire circumference on a reference plate, and to set the tire into relative rotation about its axis XX' with respect to said image acquisition means.

This device also comprises means for opening and for holding the second bead, said means comprising two internal holding rollers which are disposed circumferentially in a contiguous manner with respect to one another, have a generally radial axis and are able to come into contact with the internal side of said second bead, and at least one external holding roller which has a generally radial axis, is disposed substantially in the middle of the angular sector formed by the two internal holding rollers and is able to come into abutment against the external part of said second bead, the internal and external holding rollers being mounted so as to rotate as one about the axis XX' of said image acquisition means.

The centring means comprise locking means which, by holding the first bead around its entire circumference on said reference plate, make it possible to position the tire geometrically with respect to a mechanical reference and to keep the rotation axis of the tire in a fixed position coincident with the rotation axis of the reference plate during the inspection period. The centring means also make it possible to set the tire in relative rotation with respect to the internal and external holding rollers and with respect to the internal image acquisition means. During this movement, the second bead rolls on the internal and external holding rollers and, on account of the particular disposition of said rollers, the second bead moves into an open position between three fixed points with respect to the reference plate, said points imposing a predetermined and constant geometric path on said second bead.

By judiciously positioning the image acquisition means such as to acquire an image of an inner angular portion centered approximately on the middle of the angular sector formed by the two internal holding rollers, the image acquired is entirely unobstructed by the presence of the holding or lifting means. In this way, by making the tire execute a complete rotation about its axis with respect to the image acquisition means, it is possible to acquire a complete image of the internal surface of the tire without being subject to the drawbacks cited above in relation to the means described in the prior art. Preferably, and for greater convenience, the image acquisition means and the internal and external holding rollers are unable to rotate about the axis XX'.

BRIEF DESCRIPTION OF THE DRAWINGS

The following description relates to a preferred exemplary embodiment of the invention and is based on FIGS. 1 to 9, in which.

DETAILED DESCRIPTION OF THE DRAWINGS

Figure 1:
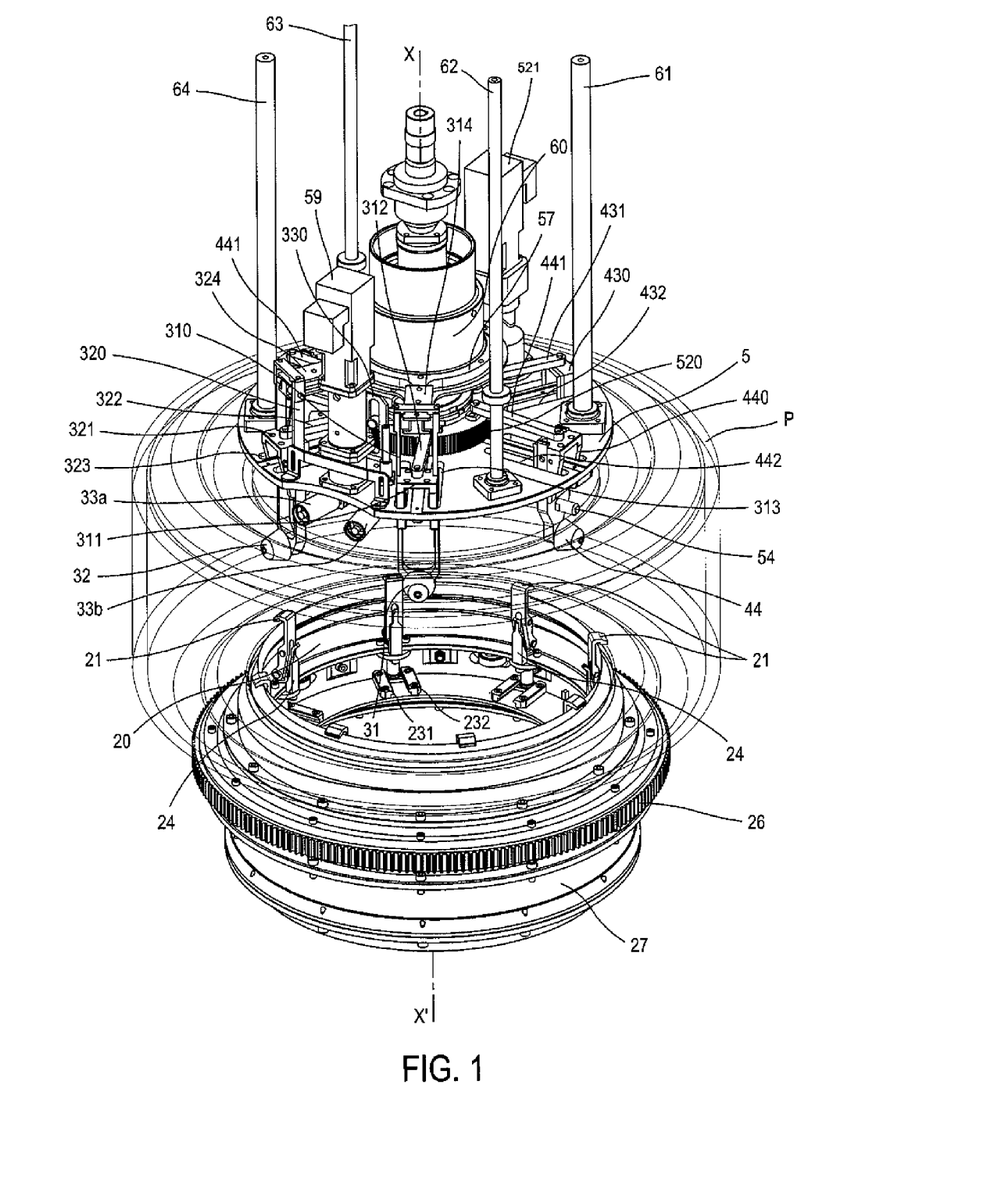
FIG. 1 shows a general perspective view of the device from the front.
Figure 2:
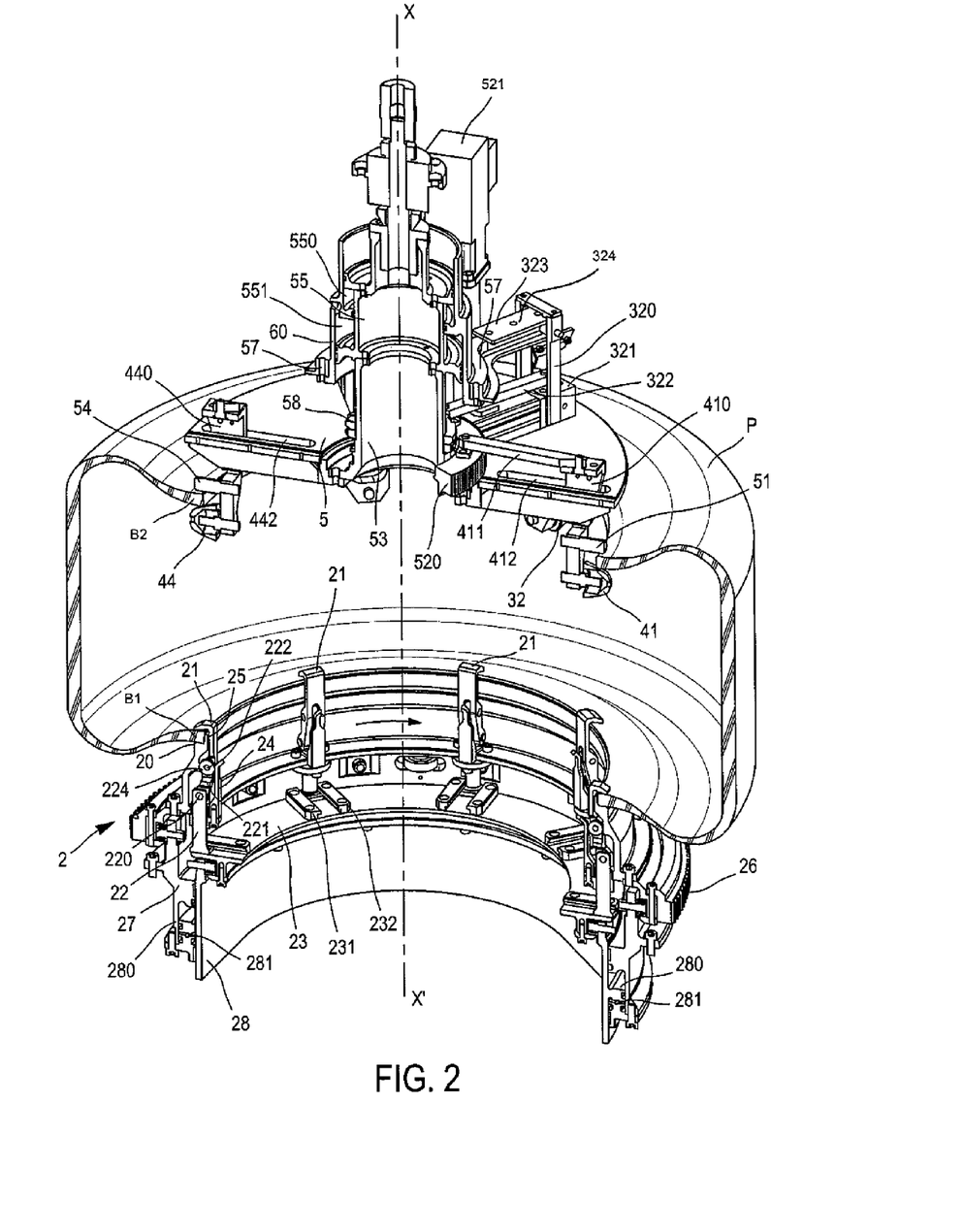
FIG. 2 shows a perspective cutaway view of the device from the rear.
Figure 3:
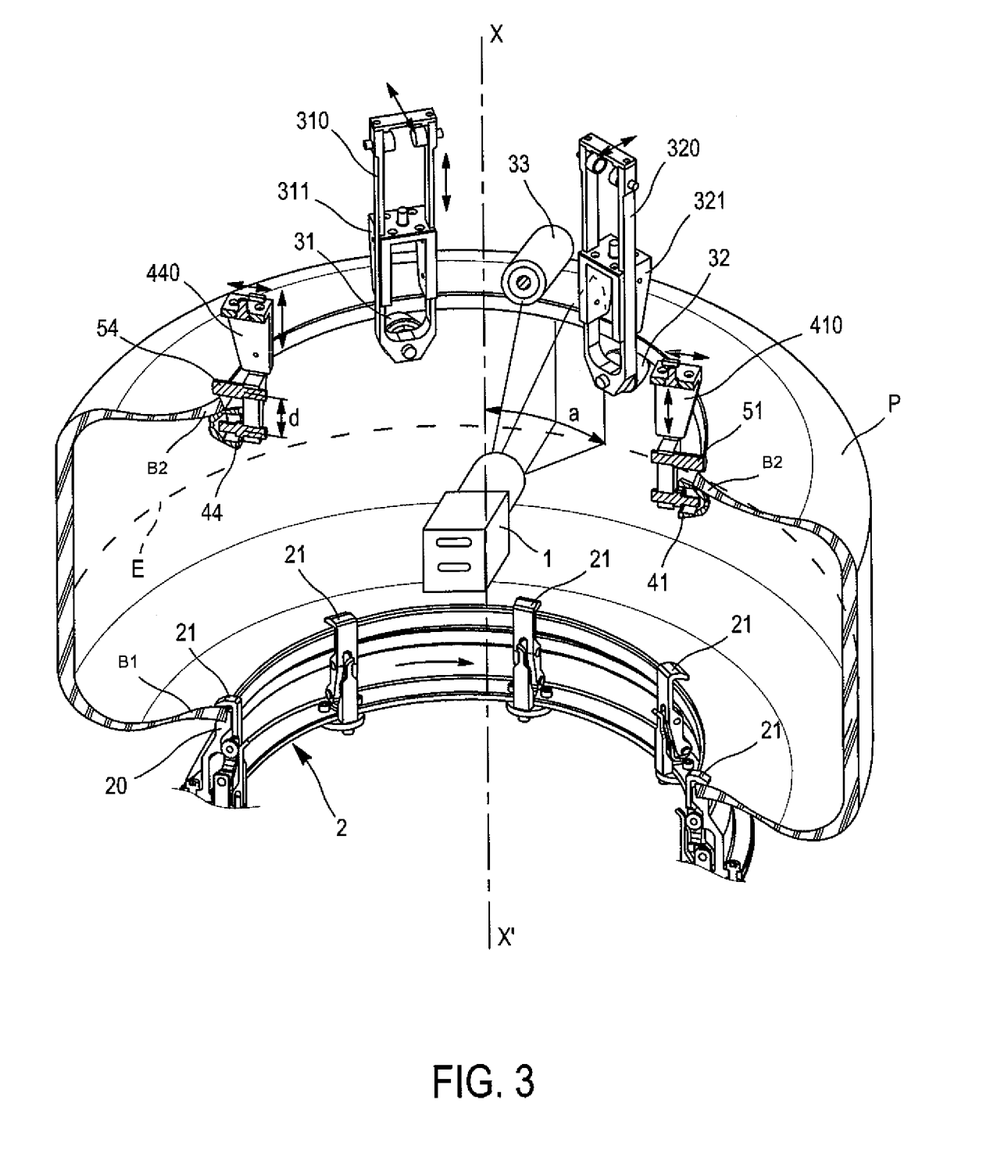
FIG. 3 shows a simplified perspective cutaway view of the device from the rear.

The device in FIGS. 1 and 2 shows the main members that form the device according to a preferred embodiment of the invention.

In this representation, the tire P, of axis XX', is mounted on a centring means 2. This centring means comprises a rim 20, the shape of which is adapted to the level of the seat 25 for receiving the first bead B1 of the tire P.

Hooks 21, which are distributed around the circumference of the rim 20 and pivot about a pin 222, keep the first bead B1 in position around its entire circumference on the seat 25. The rim 20, which serves as a reference plate, is itself mounted on a support ring 27, of axis XX', connected to a framework (not shown) by bearings, such that said ring 27 can be rotated about the axis XX' by way of a motorized pinion (not shown) engaged with a circular rack 26 mounted on the radially outer periphery of the ring 27. The axis of the rim is geometrically fixed with respect to the frame.

An annular actuator 28 is mounted inside the support ring 27 and moves axially along the axis XX' when the pneumatic pressure in relation to the inside of airtight annular chambers 280 and 281 is varied.

The annular actuator 28 supports a circular plate 23 on which axial rods 22 are mounted by way of slides 231 and 232, allowing the radial position of the axial rods 22 to be adjusted.

Figure 7:
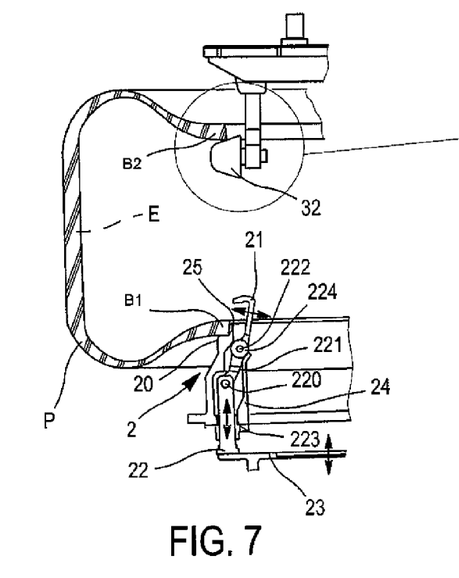
FIGS. 7, 8 and 9 show sectional views of the device for locking the first bead on the centring means.
Figure 8:
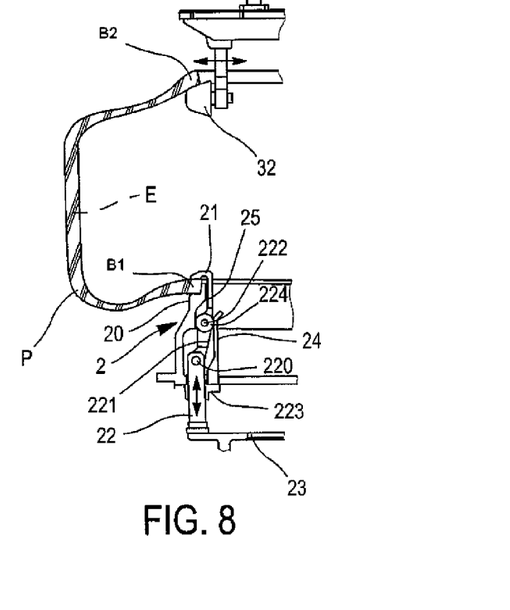
Figure 9:
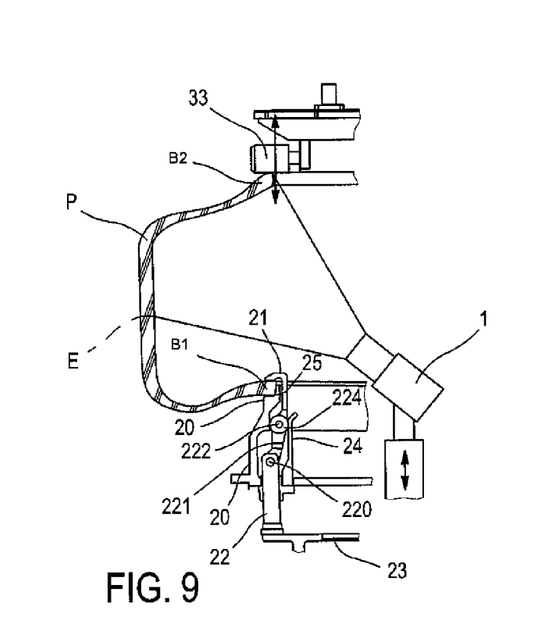

The axial rods 22 are connected to an arm 221 via a pin 220, as is illustrated in FIGS. 7, 8 and 9, which show more clearly the movement of the hooks 21. The arm 221 is connected to the hook 21 via a pin 222. The pins 220 and 222 allow the arm 221 and the hook 21 to move in a radial plane. The pin 222 has a caster 224, the movement of which is guided in a path delimited by the radially inner part of the rim 20 and by the radially outer surface of a guide arm 24. The guide arm 24 is connected to the rim 20 by a circular ring 223 that has cutouts through which the axial rods 22 slide freely in the axial direction.

The shape of the radially inner surface of the rim 20 and that of the radially outer surface of the guide arm 24 are matched to as to cooperate in order to force the movement path of the caster 224 and of the hook 21 into a radial plane, under the action of the up and down movement of the annular actuator 28 and the axial rods 22, in a manner transmitted to the hook by the arm 221.

In the top position of the plate 23, corresponding to the pressurization of the annular chamber 281, as is shown in FIG. 7, the hook 21 is tilted radially inwards about the pin 222 so as to release the first bead B1 and allow the tire to be removed from the rim 20. In the bottom position, corresponding to the pressurization of the annular chamber 280, as is illustrated in FIG. 8, the hook 21 is engaged all around the circumference of the first bead B1 so as to keep it securely applied to the seat 25 of the rim 20.

When the tire P is held on the rim 20, the axis of the tire corresponds to the rotation axis XX' of the centring means, as described above. The rotation of the tire about the axis XX' is brought about by actuating the motorized pinion acting on the rack 26.

Since the tire is held securely on the rim 20, its rotation axis remains coincident with the rotation axis of the rim, irrespective of the axial movements that occur on the second bead B2 during the opening of said second bead B2.

Figure 4:
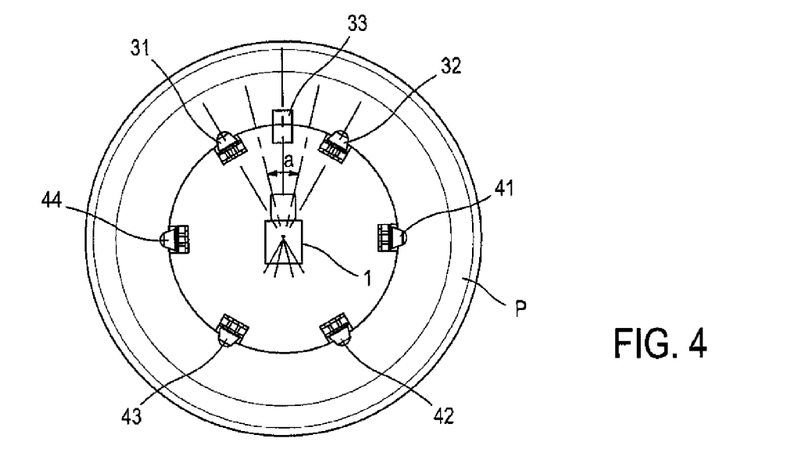
FIGS. 4, 5 and 6 respectively show a bottom view and sectional views of the device.
Figure 5:
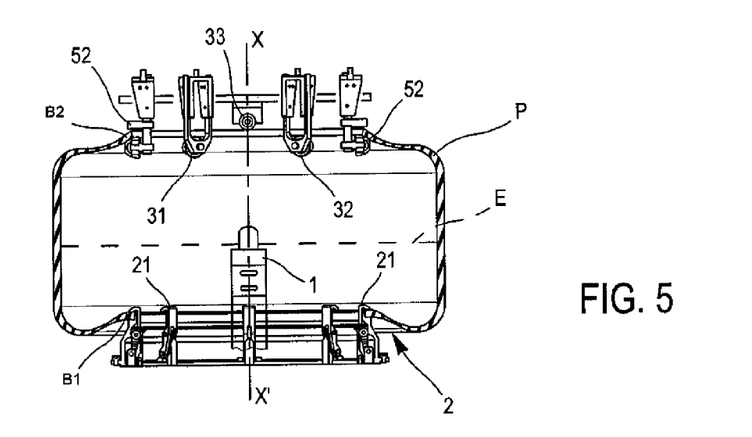
Figure 6:
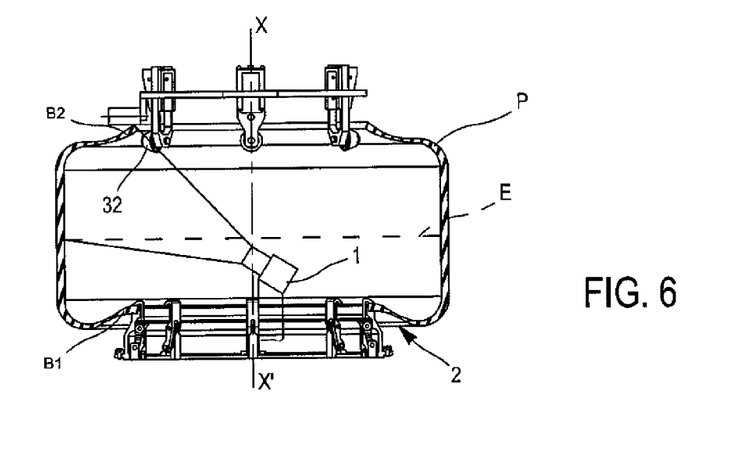

FIGS. 4 to 6 show the respective positions of the internal holding rollers 31 and 32 and the external holding roller 33. These rollers are free to rotate about their respective axes, which are oriented in the radial direction.

The internal holding rollers are able to move between a retracted position, in which they are moved back radially towards the axis XX' so as to enable the removal of the tire, and an extended position, in which they come into contact with the internal part of the second bead B2, as is illustrated in FIGS. 4 to 6.

The external holding roller 33, which comes into abutment against the outer part of the second bead B2, is disposed approximately in the middle of the angular sector formed by the two internal holding rollers 31 and 32. Angular sector is understood to mean the obtuse angle formed by the radii passing through the axis XX' and connecting the two internal holding rollers, as is illustrated in FIG. 4. The axis of the external holding roller 33 is then positioned substantially in the radial plane that passes through the bisector of the angle formed by the two internal holding rollers. This roller is disposed on the plate 5, radially plumb with the second bead B2.

The image acquisition means 1 pass axially into the space inside the tire through the internal duct in the annular actuator 28 and in the rim 20. These means are formed of one or more cameras and a lighting means. The image acquisition means are able to acquire, as required, the two- or three-dimensional image of the internal surface of the tire. Consequently, the camera or cameras are disposed so as to acquire an image of an angular region of angle a of said internal surface, such that the imaging field is centered approximately on the angular sector formed by the two internal holding rollers 31 and 32. The disposition of the internal holding rollers is then adjusted so that they are positioned outside the imaging field of the camera.

In practice, and with reference to FIGS. 5 and 6, the acquisition means are formed by a lighting means of the laser or slot-light type that forms a ray of light located in a radial plane, the intersection of which with the internal surface forms a radial line. This radial line is then positioned in the middle of the angular sector formed by the two external holding rollers. The image of the surface is obtained by placing alongside one another the images of the illuminated line by making the tire execute a complete rotation with respect to the image acquisition means 1.

According to a preferred embodiment of the invention, the image acquisition means 1 and the internal and external holding rollers 31, 32, 33 are unable to rotate with respect to the axis XX', and the tire is rotated about the axis XX' by the centring means 2. Alternatively, it is conceivable to set the image acquisition means and the internal and external holding rollers in rotation about the axis XX' and to keep the tire in a fixed position. It will be seen that this solution complicates the driving and support mechanisms which will be described below.

According to another embodiment of the invention, the lighting means are directed at just the part between the equator E and the second bead B2. This is because the hooks 21 conceal a part of the internal surface. It is then necessary to perform two imaging operations in order to have the complete image of the internal surface, as will be explained in more detail below.

An alternative embodiment of the invention provides for two external holding rollers 33a and 33b, as is illustrated in FIG. 1. In this particular case, the external holding rollers are positioned symmetrically with respect to the radial plane that passes through the bisector of the angle formed by the internal holding rollers 31 and 32. This variant embodiment makes it possible, by judiciously orienting the camera, to image the upper part of the second bead B2. To this end, it is advisable to locate the slot light in the middle of the angular sector formed by the two external holding rollers 33a and 33b.

Disposed on the circumferential sector complementary to the sector occupied by the internal holding rollers and the external holding roller(s) 33 are one or more lifting rollers 41, 42, 43, 44. These rollers are free to rotate about an approximately radial axis and are able to come into contact with the internal side of the second bead B2 and, by an axial movement, to lift the rest of said second bead B2 in order to minimize the axial movements of the second bead B2 during the operation of taking imaging and forming the internal image.

Figure 5A:
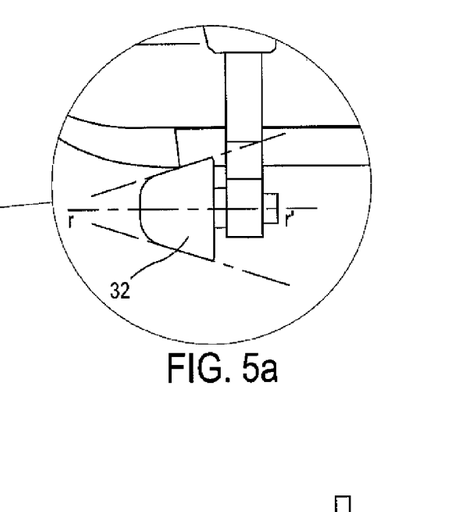

The particular shape of an internal holding roller can be seen in FIG. 5a, the inset to FIG. 7. This roller has a generally frustoconical shape, with the tip being oriented radially outwards. This particular arrangement makes it possible to support the second bead B2 without damaging it during the lifting phase, during which the second bead B2 rotates about the rigid bead reinforcing wire. This particular geometry applies to the lifting rollers 41, 42, 43 and 44 for the same reasons.

Lugs 51, 52 (not shown), 53 (not shown), 54 are disposed axially towards the outside with respect to the lifting rollers, from which they are offset by an experimentally determined distance (d). In practice, this distance corresponds to around four or five times the thickness of the second bead B2. These lugs are intended to return the second bead B2 to the closed position at the end of the imaging cycle.

FIGS. 1 and 2 show the means for supporting and operating the holding rollers and the lifting rollers.

A plate 5, which is able to move axially under the action of an axial lead screw actuated by a motor (not shown), is connected to a fixed framework by way of guide rods 61, 62, 63, 64. The plate 5 carries all of the means that support the holding rollers 31, 32 and 33 and lifting rollers 41, 42, 43, 44.

The internal holding rollers 31 and 32 are mounted on mobile frames 310, 320 which are themselves mounted such as to be able to slide in the axial direction on supports 311 and 321, respectively.

The supports 311 and 321 slide freely in slots 313, 323 and are able to move radially under the action of connecting rods 312 and 322, respectively, which are rotated by a toothed annular crown gear 520 under the action of a motor 521.

The central part of the plate 5 carries a space holder 53, about which the toothed annular crown gear 520 rotates, and on which there is mounted a double-acting annular actuator, comprising a fixed part 55 mounted on the space holder 53 and a part 60, that is able to move axially in one direction or the other under the effect of the pressurization of the airtight chambers 550 or 551. The ascent or descent of the mobile part 60 of the annular actuator causes the frames 310 and 320 to ascend or descend along the supports 311 and 321 by way of an annular plate 57 and a radial arm 314 and 324. In this way, it is possible to control the ascent and descent of the internal holding rollers 31 and 32 with respect to the plate 5.

The external holding roller(s) (33 or 33a and 33b) are supported by a frame 330 and are able to move axially with respect to the plate 5 under the action of the motor 59. In this way, it is possible to move the external holding roller(s) in just the axial direction with respect to the plate 5. However, radial adjustment can be provided in order to dimensionally adapt the position of the external holding rollers.

The lifting rollers 41, 42, 43 and 44 are supported by a bracket 410, 420 (not shown), 430, 440. In the same way as the supports 310 and 320, the brackets 410, 420 (not shown), 430 and 440 are mounted on the plate 5 and slide freely in slots 412, 422 (not shown), 432 and 442. These brackets are able to move radially under the action of connecting rods 411, 421 (not shown), 431 and 441, respectively, which are rotated by an annular crown gear 520 under the action of the motor 521. In this way, the radial movement of the internal holding rollers 31 and 32 and of the lifting rollers 41, 42, 43 and 44 is controlled simultaneously by the action of the motor 521.

The operation of the device according to the invention provides the following sequences.

Firstly, the tire is placed on the centring means 2 such that the first bead B1 is fitted on the seat 25 of the rim 20. The hooks 21 are then closed under the action of the annular actuator 28.

Next, the plate 5 is lowered in the direction of the second bead B2. During this manoeuvre, the internal holding rollers 31 and 32 and the lifting rollers 41, 42, 43, 44 are in a radially folded back position so as to enable said rollers to pass into the space inside the tire at the level of the second bead B2. The plate 5 is lowered such that the lifting rollers 41, 42, 43 and 44 are located in a meridian plane positioned inside the volume of the tire and such that the lugs 51, 52 (not shown), 53 (not shown) and 54 are located in a meridian plane outside the internal volume of the tire.

In the following sequence, the motor 521 is activated and the internal holding rollers 31 and 32 and the lifting rollers 41, 42, 43 and 44 are extended radially such that said rollers are disposed radially under the second bead B2 to be lifted B2.

The internal holding rollers 31 and 32 are then lowered axially with respect to the plate by lowering the mobile part 60 of the annular actuator such that said holding rollers 31 and 32 are disposed in an axially inner meridian plane with respect to the meridian plane on which the lifting rollers 41, 42, 43 and 44 are placed.

By axially lifting the plate 5, the lifting rollers 41, 42, 43 and 44 come into contact with the inner part of the second bead B2 and lift it with respect to the equator E of the tire over a part of its circumference. The partial lifting movement is stopped when the second bead reaches a predetermined axial opening level depending on the size of the tire.

The mobile part 60 of the annular actuator is lifted axially so as to lift the complementary part of the second bead B2 in the axial direction, under the action of the internal holding rollers 31 and 32, with respect to the equator E of the tire. The holding rollers are then positioned approximately in the same meridian plane as the lifting rollers 41, 42, 43 and 44.

Although it would be quite possible to lift the second bead B2 by bringing the holding rollers 31 and 32 and the lifting rollers 41, 42, 43 and 44 simultaneously into contact with the internal part of the second bead B2, it has been shown that this two-part action is rendered more or less necessary if it is intended to reduce the forces connected with axially opening the second bead B2.

In order to ensure good dimensional stability of the tire, it is possible to slightly lift the plate 5 in the axial direction so as to place the tire under tension.

The external holding roller (33) or rollers (33a, 33b) are then lowered by actuating the motor 59 so as to bring said external rollers into contact with the outer part of the second bead B2. The second bead B2 is then positioned simultaneously in contact with the internal holding rollers 31 and 32 and the external holding roller(s) 33 or 33a and 33b.

The internal image acquisition means 1 are introduced axially so as to illuminate the portion of the internal space that is located between the equator E and the second bead B2.

The following step consists in setting the tire in rotation about the axis XX' by activating the motor (not shown) that controls the pinions engaged with the rack 26.

The second bead B2 rolls on the internal holding rollers 31 and 32 and on the external holding roller 33 such that the position of the internal surface illuminated by the internal image acquisition means is strictly constant with respect to said acquisition means when the tire executes a rotation through 360° about the axis XX'.

Once the image of the internal surface between the equator E and the second bead B2 has been acquired, the internal image acquisition means 1 are withdrawn axially.

The external holding roller 33 is lifted with the aid of the motor 59, then the plate 5 is lowered axially so as to bring the lugs 51, 52 (not shown), 53 (not shown) and 54 into contact with the axially outer part of the second bead B2 and the axial movement of the plate is followed as far as a predetermined level at which the second bead B2 is completely closed.

The internal holding rollers 31 and 32 and the lifting rollers 41, 42, 43 and 44 are retracted radially by activating the motor 521, and the plate 5 is lifted in order to free the space above the second bead B2.

The hooks 21 are unlocked so as to release the tire and the tire is removed from said device.

It will be seen that the device that is the subject of the present description allows the acquisition of the image of an internal half. It is then necessary to turn the tire over and to restart the sequence of operations as described above in order to acquire the image of the second half of the internal surface. The complete image of the internal surface is obtained by placing the first and second images alongside one another. On account of the great geometric precision in the positioning of the tire during the internal image acquisition phase, image calibration operations are reduced to a single operation of bringing the starting azimuth of the two image halves into correspondence.

It will be seen in conclusion that the embodiment of the invention that is the subject of the present description can be subject to numerous variants, both in the construction of the device and in the sequencing of the phases of its implementation, without it being necessary to depart from the general principles that are the subject of the present description.

The invention claimed is:

1. A device for inspecting an internal surface of a tire located between a first and a second bead of the tire, comprising:
   an image acquisition means for acquiring an image of the internal surface of the tire, said image acquisition means comprising a lighting means and one or more cameras and being able to pass into a space inside the tire and to produce the image of an angular region of given angle of the internal surface of the tire;
   centering means able to lock the first bead around its entire circumference on a reference plate, and able to set the tire into relative rotation about its axis XX' with respect to said image acquisition means; and
   means for opening and for holding the second bead comprising;
      two internal holding rollers which are disposed circumferentially on a lifting plate in a contiguous manner with respect to one another and which have a generally radial axis,
      at least one external holding roller which has a generally radial axis, which is disposed substantially in the middle of an angular sector formed by the two internal holding rollers, and which is able to come into abutment against an external part of said second bead, wherein the internal rollers and the at least one external holding roller are mounted so as to rotate as one about the axis XX' of said image acquisition means,
      one or more lifting rollers which have a generally radial axis and move radially between a refracted position and an extended position in which said one or more lifting rollers are able to come into contact with the axially internal side of said second bead and to move in an axial direction so as to move said second bead away from an equator of the tire, said one or more lifting rollers being disposed circumferentially on a complementary part of the angular sector occupied by the internal holding rollers.

2. The device according to claim 1, comprising at least two external holding rollers spaced apart angularly.

3. The device according to claim 1, wherein the internal holding rollers move between a refracted position and an extended position in which said internal holding rollers are able to come into contact with the internal side of the second bead and to move in an axial direction so as to move away from an equator of the tire and then to retain said second bead in position.

4. The device according to claim 1, wherein the image acquisition means are positioned so as to acquire the image of an angular portion of the internal surface of the tire centered on the middle of the angular sector formed by the axes of the two internal holding rollers.

5. The device according to claim 1, wherein the image acquisition means and the internal holding rollers and the at least one external holding roller are unable to rotate about the axis XX', and in which the tire is rotated about its axis XX' by said centering means.

6. The device according to claim 1, further comprising lugs which are disposed axially on the exterior of the second bead at a given distance from the one or more lifting rollers and are able to carry out an axial movement so as to return the second bead to the closed position.

7. The device according to claim 1, wherein the internal holding rollers and the one or more lifting rollers have an approximately frustoconical radial profile.

8. The device according to claim 1, wherein the tire centering means comprise a centering ring, which forms the reference plate and is able to receive the first bead, and retractable hooks for locking said second bead on said centering ring, said hooks being placed at regular intervals around the entire circumference of said centering ring.

9. The device according to claim 8, wherein the centering ring has a central passage allowing the image acquisition means to access an interior of the tire.

10. The device according to claim 1, wherein the image acquisition means comprise a laser lighting means for illuminating a radial line and a camera able to capture light reflected by the internal surface of the tire, and in which said radial line is centered approximately on the middle of the angular sector formed by the pair of internal holding rollers.

11. A method for inspecting the internal part of the tire comprising the first and the second bead with the aid of the device according to claim 1, comprising, in sequence:
- the tire is fitted on the device;
- the centering means are activated so as to lock the first bead on the reference plate;
- the internal holding rollers and the lifting rollers are retracted radially;
- the reference plate is moved in a direction parallel to the axis XX' so as to move the first bead away from the second bead;
- the internal holding rollers and the lifting rollers are extended radially into the space inside the tire;
- the lifting plate is moved in a direction parallel to the axis XX' as to move the second bead away from the first bead;
- the at least one external holding roller is/are moved so as to hold the second bead securely between the two internal holding rollers and the at least one external holding roller;
- the image acquisition means are introduced into the space inside the tire;
- the centering means rotates so that the tire rotates about the axis XX' with respect to the image acquisition means; and
- the image of the internal surface of the tire is acquired by the image acquisition means.

12. The inspection method according to claim 11, wherein the image of the internal surface of the tire is obtained by rotating the tire through 360° with respect to the image acquisition means.

13. The inspection method according to claim 11, wherein, after the internal holding rollers and the lifting rollers have been extended,
- the internal holding rollers are moved axially with respect to the lifting rollers toward the equator of the tire,
- a portion of a circumference of the second bead is moved by moving the lifting plate in a direction away from the equator of the tire and by bringing the lifting rollers into contact with the axially inner part of the second bead up to a given distance, and
- the internal holding rollers are moved so that a remainder of the circumference of said second bead is moved in the direction away from the equator of the tire.

14. The inspection method according to claim 13, wherein:
- a first image is produced of a first half of the internal surface of the tire between the second bead and the equator of the tire,
- the tire is turned over,
- a second image is produced of a second half of the internal surface of the tire between the first bead and the equator of the tire, and
- the image of the internal surface is obtained by placing the first and the second image alongside one another.

\* \* \* \* \*